United States Patent
Gannoe et al.

(10) Patent No.: US 8,092,482 B2
(45) Date of Patent: Jan. 10, 2012

(54) STENTED ANCHORING OF GASTRIC SPACE-OCCUPYING DEVICES

(75) Inventors: James Gannoe, Redwood City, CA (US); Federico Gutierrez, Pacifica, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 898 days.

(21) Appl. No.: 11/406,914

(22) Filed: Apr. 19, 2006

(65) Prior Publication Data

US 2006/0190019 A1    Aug. 24, 2006

Related U.S. Application Data

(63) Continuation of application No. 10/233,236, filed on Aug. 30, 2002, now Pat. No. 7,033,384.

(51) Int. Cl.
*A61M 29/00* (2006.01)
(52) U.S. Cl. ......... 606/194; 606/192; 606/193; 606/154
(58) Field of Classification Search .................... 600/37; 606/153, 154, 192–194; 623/1.11; 604/509
See application file for complete search history.

(56) References Cited

U.S. PATENT DOCUMENTS

| | | | |
|---|---|---|---|
| 2,108,206 A | 2/1938 | Meeker | |
| 2,508,690 A | 7/1948 | Schmerl | |
| 3,395,710 A | 8/1968 | Stratton et al. | |
| 3,986,493 A | 10/1976 | Hendren, III | |
| 4,057,065 A | 11/1977 | Thow | |
| 4,133,315 A | 1/1979 | Berman et al. | |
| 4,134,405 A | 1/1979 | Smit | |
| 4,198,982 A | 4/1980 | Fortner et al. | |
| 4,246,893 A | 1/1981 | Berson | |
| 4,315,509 A | 2/1982 | Smit | |
| 4,343,066 A | 8/1982 | Lance | |
| 4,402,445 A | 9/1983 | Green | |
| 4,416,267 A * | 11/1983 | Garren et al. | 128/898 |
| 4,458,681 A | 7/1984 | Hopkins | |
| 4,485,805 A | 12/1984 | Foster, Jr. | |
| 4,501,264 A * | 2/1985 | Rockey | 128/898 |
| 4,547,192 A | 10/1985 | Brodsky et al. | |

(Continued)

FOREIGN PATENT DOCUMENTS

EP    0 137 878 A1    4/1985

(Continued)

OTHER PUBLICATIONS

T. M. Boyle et al., "Small Intestinal Obstruction Secondary to Obturation by a Garren Gastric Bubble", *The Am. J. of Gastroenterology*, vol. 82, No. 1, 1987, pp. 51-53.

(Continued)

*Primary Examiner* — Corrine M McDermott
*Assistant Examiner* — Gregory Anderson
(74) *Attorney, Agent, or Firm* — Nutter McClennen & Fish LLP

(57) ABSTRACT

Gastric space occupying devices are provided that include a stent configured for deployment in the gastrointestinal tract of a patient, and in particular, for deployment in the esophagus or the stomach. Secured to the stent is an expandable member that is adapted to reside within the patient's stomach. When expanded, the expandable member occupies a predefined volume within the patient's stomach and is further tethered to the deployed stent, thereby retaining or anchoring the expandable member within the stomach. Methods and systems for the deploying the space occupying devices are also provided.

8 Claims, 2 Drawing Sheets

U.S. PATENT DOCUMENTS

| | | |
|---|---|---|
| 4,558,699 A | 12/1985 | Bashour |
| 4,592,339 A | 6/1986 | Kuzmak et al. |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,641,653 A | 2/1987 | Rockey |
| 4,646,722 A | 3/1987 | Silverstein et al. |
| 4,648,383 A | 3/1987 | Angelchik |
| 4,694,827 A | 9/1987 | Weiner et al. |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,773,393 A | 9/1988 | Haber et al. |
| 4,790,294 A | 12/1988 | Allred, III et al. |
| 4,803,985 A | 2/1989 | Hill |
| 4,841,888 A | 6/1989 | Mills et al. |
| 4,899,747 A | 2/1990 | Garren et al. |
| 4,905,693 A | 3/1990 | Ravo |
| 4,927,428 A | 5/1990 | Richards |
| 4,969,474 A | 11/1990 | Schwarz |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,156,609 A | 10/1992 | Nakao et al. |
| 5,171,233 A | 12/1992 | Amplatz et al. |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,246,456 A | 9/1993 | Wilkinson |
| 5,250,058 A | 10/1993 | Miller et al. |
| 5,254,126 A | 10/1993 | Filipi et al. |
| 5,259,399 A | 11/1993 | Brown |
| 5,261,920 A | 11/1993 | Main et al. |
| 5,263,629 A | 11/1993 | Trumbull et al. |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,330,486 A | 7/1994 | Wilk |
| 5,330,503 A | 7/1994 | Yoon |
| 5,331,975 A | 7/1994 | Bonutti |
| 5,334,209 A | 8/1994 | Yoon |
| 5,334,210 A | 8/1994 | Gianturco |
| 5,345,949 A | 9/1994 | Shlain |
| 5,346,501 A | 9/1994 | Regula et al. |
| 5,355,897 A | 10/1994 | Pietrafitta et al. |
| 5,376,095 A | 12/1994 | Ortiz |
| 5,382,231 A | 1/1995 | Shlain |
| 5,403,312 A | 4/1995 | Yates et al. |
| 5,403,326 A | 4/1995 | Harrison et al. |
| 5,411,508 A | 5/1995 | Bessler et al. |
| 5,433,721 A | 7/1995 | Hooven et al. |
| 5,437,291 A | 8/1995 | Pasricha et al. |
| 5,449,368 A | 9/1995 | Kuzmak |
| 5,452,837 A | 9/1995 | Williamson, IV et al. |
| 5,458,131 A | 10/1995 | Wilk |
| 5,465,894 A | 11/1995 | Clark et al. |
| 5,467,911 A | 11/1995 | Tsuruta et al. |
| 5,486,183 A | 1/1996 | Middleman et al. |
| 5,489,058 A | 2/1996 | Plyley et al. |
| 5,503,635 A | 4/1996 | Sauer et al. |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos et al. |
| 5,685,868 A | 11/1997 | Lundquist |
| 5,690,656 A | 11/1997 | Cope et al. |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,730 A | 5/1998 | Swain et al. |
| 5,766,216 A | 6/1998 | Gangal et al. |
| 5,776,054 A | 7/1998 | Bobra |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |
| 5,833,690 A | 11/1998 | Yates et al. |
| 5,836,311 A | 11/1998 | Borst et al. |
| 5,839,639 A | 11/1998 | Sauer et al. |
| 5,860,581 A | 1/1999 | Robertson et al. |
| 5,861,036 A | 1/1999 | Godin |
| 5,868,141 A | 2/1999 | Ellias |
| 5,868,760 A | 2/1999 | McGuckin, Jr. |
| 5,876,448 A | 3/1999 | Thompson et al. |
| 5,879,371 A | 3/1999 | Gardiner et al. |
| 5,887,594 A | 3/1999 | LoCicero, III |
| 5,888,196 A | 3/1999 | Bonutti |
| 5,897,534 A | 4/1999 | Heim et al. |
| 5,897,562 A | 4/1999 | Bolanos et al. |
| 5,902,333 A | 5/1999 | Roberts et al. |
| 5,906,625 A | 5/1999 | Bito et al. |
| 5,910,105 A | 6/1999 | Swain et al. |
| 5,910,149 A | 6/1999 | Kuzmak |
| 5,921,993 A | 7/1999 | Yoon |
| 5,927,284 A | 7/1999 | Borst et al. |
| 5,928,264 A | 7/1999 | Sugarbaker et al. |
| 5,935,107 A | 8/1999 | Taylor et al. |
| 5,938,669 A | 8/1999 | Klaiber et al. |
| 5,947,983 A | 9/1999 | Solar et al. |
| 5,964,772 A | 10/1999 | Bolduc et al. |
| 5,964,782 A | 10/1999 | Lafontaine et al. |
| 5,972,001 A | 10/1999 | Yoon |
| 5,972,002 A | 10/1999 | Bark et al. |
| 5,976,161 A | 11/1999 | Kirsch et al. |
| 5,980,537 A | 11/1999 | Ouchi |
| 5,993,464 A | 11/1999 | Knodel |
| 5,993,473 A | 11/1999 | Chan et al. |
| 6,013,854 A | 1/2000 | Moriuchi |
| 6,015,378 A | 1/2000 | Borst et al. |
| 6,030,364 A | 2/2000 | Durgin et al. |
| 6,030,392 A | 2/2000 | Dakov |
| 6,042,538 A | 3/2000 | Puskas |
| 6,044,847 A | 4/2000 | Carter et al. |
| 6,067,991 A | 5/2000 | Forsell |
| 6,074,343 A | 6/2000 | Nathanson et al. |
| 6,083,241 A | 7/2000 | Longo et al. |
| 6,086,600 A | 7/2000 | Kortenbach |

| | | |
|---|---|---|
| 6,113,609 A | 9/2000 | Adams |
| 6,119,913 A | 9/2000 | Adams et al. |
| 6,120,513 A | 9/2000 | Bailey et al. |
| 6,136,006 A | 10/2000 | Johnson et al. |
| 6,159,146 A | 12/2000 | El Gazayerli |
| 6,159,195 A | 12/2000 | Ha et al. |
| 6,165,183 A | 12/2000 | Kuehn et al. |
| 6,179,195 B1 | 1/2001 | Adams et al. |
| 6,186,942 B1 | 2/2001 | Sullivan et al. |
| 6,186,985 B1 | 2/2001 | Snow |
| 6,197,022 B1 | 3/2001 | Baker |
| 6,200,318 B1 | 3/2001 | Har-Shai et al. |
| 6,206,822 B1 | 3/2001 | Foley et al. |
| 6,206,893 B1 | 3/2001 | Klein et al. |
| 6,224,614 B1 | 5/2001 | Yoon |
| 6,231,561 B1 | 5/2001 | Frazier et al. |
| 6,248,058 B1 | 6/2001 | Silverman et al. |
| 6,254,642 B1 | 7/2001 | Taylor |
| 6,273,897 B1 | 8/2001 | Dalessandro et al. |
| 6,279,809 B1 | 8/2001 | Nicolo |
| 6,290,674 B1 | 9/2001 | Roue et al. |
| 6,293,923 B1 | 9/2001 | Yachia et al. |
| 6,302,917 B1 | 10/2001 | Dua et al. |
| 6,312,437 B1 | 11/2001 | Kortenbach |
| 6,328,689 B1 | 12/2001 | Gonzalez et al. |
| 6,338,345 B1 | 1/2002 | Johnson et al. |
| 6,358,197 B1 | 3/2002 | Silverman et al. |
| 6,379,366 B1 | 4/2002 | Fleischmann et al. |
| 6,387,104 B1 | 5/2002 | Pugsley, Jr. et al. |
| 6,398,795 B1 | 6/2002 | McAlister et al. |
| 6,416,535 B1 | 7/2002 | Lazarus |
| 6,423,087 B1 | 7/2002 | Sawada |
| 6,432,040 B1 | 8/2002 | Meah |
| 6,447,533 B1 | 9/2002 | Adams |
| 6,460,543 B1 | 10/2002 | Forsell |
| 6,464,625 B2 | 10/2002 | Ganz |
| 6,475,136 B1 | 11/2002 | Forsell |
| 6,491,707 B2 | 12/2002 | Makower et al. |
| 6,494,888 B1 | 12/2002 | Laufer et al. |
| 6,506,196 B1 | 1/2003 | Laufer |
| 6,506,202 B1 | 1/2003 | Dutta et al. |
| 6,535,764 B2 | 3/2003 | Imran et al. |
| 6,540,789 B1 | 4/2003 | Silverman et al. |
| 6,551,310 B1 | 4/2003 | Ganz et al. |
| 6,554,844 B2 | 4/2003 | Lee et al. |
| 6,558,400 B2 | 5/2003 | Deem et al. |
| 6,561,969 B2 | 5/2003 | Frazier et al. |
| 6,572,629 B2 | 6/2003 | Kalloo et al. |
| 6,592,596 B1 | 7/2003 | Geitz |
| 6,605,037 B1 | 8/2003 | Moll et al. |
| 6,605,110 B2 * | 8/2003 | Harrison ............ 623/1.15 |
| 6,626,899 B2 | 9/2003 | Houser et al. |
| 6,632,227 B2 | 10/2003 | Adams |
| 6,663,598 B1 | 12/2003 | Carrillo, Jr. et al. |
| 6,663,639 B1 | 12/2003 | Laufer et al. |
| 6,663,640 B2 | 12/2003 | Kortenbach |
| 6,675,809 B2 * | 1/2004 | Stack et al. .......... 128/898 |
| 6,682,520 B2 | 1/2004 | Ingenito |
| 6,689,062 B1 | 2/2004 | Mesallum |
| 6,692,485 B1 | 2/2004 | Brock et al. |
| 6,716,222 B2 | 4/2004 | McAlister et al. |
| 6,733,512 B2 | 5/2004 | McGhan |
| 6,736,822 B2 | 5/2004 | McClellan et al. |
| 6,740,098 B2 | 5/2004 | Abrams et al. |
| 6,740,121 B2 | 5/2004 | Geitz |
| 6,746,489 B2 | 6/2004 | Dua et al. |
| 6,754,536 B2 | 6/2004 | Swoyer et al. |
| 6,755,849 B1 | 6/2004 | Gowda et al. |
| 6,755,869 B2 | 6/2004 | Geitz |
| 6,756,364 B2 | 6/2004 | Barbier et al. |
| 6,764,518 B2 | 7/2004 | Godin |
| 6,773,440 B2 | 8/2004 | Gannoe et al. |
| 6,773,441 B1 | 8/2004 | Laufer |
| 6,786,898 B2 | 9/2004 | Guenst |
| 6,790,214 B2 | 9/2004 | Kraemer et al. |
| 6,802,868 B2 | 10/2004 | Silverman et al. |
| 6,821,285 B2 | 11/2004 | Laufer et al. |
| 6,835,199 B2 | 12/2004 | McGuckin, Jr. et al. |
| 6,835,200 B2 | 12/2004 | Laufer et al. |
| 6,837,848 B2 | 1/2005 | Bonner et al. |
| 6,840,423 B2 | 1/2005 | Adams et al. |
| 6,845,776 B2 | 1/2005 | Stack et al. |
| 6,896,682 B1 | 5/2005 | McClellan et al. |
| 6,926,722 B2 | 8/2005 | Geitz |
| 6,966,919 B2 | 11/2005 | Sixto, Jr. et al. |
| 6,981,978 B2 | 1/2006 | Gannoe |
| 6,991,643 B2 | 1/2006 | Saadat |
| 7,020,531 B1 | 3/2006 | Colliou et al. |
| 7,025,791 B2 | 4/2006 | Levine et al. |
| 7,033,373 B2 | 4/2006 | de la Torre et al. |
| 7,033,378 B2 | 4/2006 | Smith et al. |
| 7,033,384 B2 * | 4/2006 | Gannoe et al. .............. 623/1.11 |
| 7,037,343 B2 | 5/2006 | Imran |
| 7,037,344 B2 | 5/2006 | Kagan et al. |
| 7,063,715 B2 | 6/2006 | Onuki et al. |
| 7,083,630 B2 | 8/2006 | DeVries et al. |
| 7,087,011 B2 | 8/2006 | Cabiri et al. |
| 2001/0014800 A1 | 8/2001 | Frazier et al. |
| 2001/0020190 A1 | 9/2001 | Taylor |
| 2001/0037127 A1 | 11/2001 | De Hoyos Garza |
| 2002/0022851 A1 | 2/2002 | Kalloo et al. |
| 2002/0035361 A1 | 3/2002 | Houser et al. |
| 2002/0040226 A1 | 4/2002 | Laufer et al. |
| 2002/0047036 A1 | 4/2002 | Sullivan et al. |
| 2002/0058967 A1 | 5/2002 | Jervis |
| 2002/0072761 A1 | 6/2002 | Abrams et al. |
| 2002/0077661 A1 | 6/2002 | Saadat |
| 2002/0078967 A1 | 6/2002 | Sixto, Jr. et al. |
| 2002/0082621 A1 | 6/2002 | Schurr et al. |
| 2002/0143346 A1 | 10/2002 | McGuckin, Jr. et al. |
| 2002/0165589 A1 | 11/2002 | Imran et al. |
| 2002/0183768 A1 | 12/2002 | Deem et al. |
| 2002/0193816 A1 | 12/2002 | Laufer et al. |
| 2003/0040804 A1 | 2/2003 | Stack et al. |
| 2003/0040808 A1 | 2/2003 | Stack et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0120285 A1 | 6/2003 | Kortenbach |
| 2003/0120289 A1 | 6/2003 | McGuckin, Jr. et al. |
| 2003/0132267 A1 | 7/2003 | Adams et al. |
| 2003/0158563 A1 | 8/2003 | McClellan et al. |
| 2003/0158601 A1 | 8/2003 | Silverman et al. |
| 2003/0171760 A1 | 9/2003 | Gambale |
| 2003/0208209 A1 | 11/2003 | Gambale et al. |
| 2003/0225312 A1 | 12/2003 | Suzuki et al. |
| 2004/0006351 A1 | 1/2004 | Gannoe et al. |
| 2004/0009224 A1 | 1/2004 | Miller |
| 2004/0010271 A1 | 1/2004 | Kortenbach |
| 2004/0024386 A1 | 2/2004 | Deem et al. |
| 2004/0037865 A1 | 2/2004 | Miller |
| 2004/0039452 A1 | 2/2004 | Bessler |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087977 A1 | 5/2004 | Nolan et al. |
| 2004/0089313 A1 | 5/2004 | Utley et al. |
| 2004/0092892 A1 | 5/2004 | Kagan et al. |
| 2004/0097989 A1 | 5/2004 | Molina Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |

| | | | |
|---|---|---|---|
| 2004/0148021 A1 | 7/2004 | Cartledge et al. | |
| 2004/0148034 A1 | 7/2004 | Kagan et al. | |
| 2004/0158331 A1 | 8/2004 | Stack et al. | |
| 2004/0162568 A1 | 8/2004 | Saadat et al. | |
| 2004/0167546 A1 | 8/2004 | Saadat et al. | |
| 2004/0172141 A1 | 9/2004 | Stack et al. | |
| 2004/0181242 A1 | 9/2004 | Stack et al. | |
| 2004/0193190 A1 | 9/2004 | Liddicoat et al. | |
| 2004/0225183 A1 | 11/2004 | Michlitsch et al. | |
| 2004/0225194 A1 | 11/2004 | Smith et al. | |
| 2004/0225305 A1 | 11/2004 | Ewers et al. | |
| 2005/0004681 A1* | 1/2005 | Stack et al. | 623/23.65 |
| 2005/0049718 A1 | 3/2005 | Dann et al. | |
| 2005/0055038 A1 | 3/2005 | Kelleher et al. | |
| 2005/0055039 A1 | 3/2005 | Burnett et al. | |
| 2005/0075622 A1 | 4/2005 | Levine et al. | |
| 2005/0075653 A1 | 4/2005 | Saadat et al. | |
| 2005/0080444 A1 | 4/2005 | Kraemer et al. | |
| 2005/0085787 A1 | 4/2005 | Laufer | |
| 2005/0096750 A1 | 5/2005 | Kagan et al. | |
| 2005/0119671 A1 | 6/2005 | Reydel et al. | |
| 2005/0143760 A1 | 6/2005 | Imran | |
| 2005/0148818 A1 | 7/2005 | Mesallum | |
| 2005/0149067 A1 | 7/2005 | Takemoto et al. | |
| 2005/0149114 A1 | 7/2005 | Cartledge et al. | |
| 2005/0177176 A1 | 8/2005 | Gerbi et al. | |
| 2005/0194038 A1 | 9/2005 | Brabec et al. | |
| 2005/0194294 A1 | 9/2005 | Oexle et al. | |
| 2005/0194312 A1 | 9/2005 | Niemeyer et al. | |
| 2005/0195925 A1 | 9/2005 | Traber | |
| 2005/0195944 A1 | 9/2005 | Bartels et al. | |
| 2005/0196356 A1 | 9/2005 | Leinen et al. | |
| 2005/0197540 A1 | 9/2005 | Liedtke | |
| 2005/0197622 A1 | 9/2005 | Blumenthal et al. | |
| 2005/0197684 A1 | 9/2005 | Koch | |
| 2005/0198476 A1 | 9/2005 | Gazsi et al. | |
| 2005/0203548 A1 | 9/2005 | Weller et al. | |
| 2005/0228415 A1 | 10/2005 | Gertner | |
| 2005/0256587 A1 | 11/2005 | Egan | |
| 2006/0020247 A1 | 1/2006 | Kagan et al. | |
| 2006/0020254 A1 | 1/2006 | Hoffmann | |
| 2006/0020276 A1 | 1/2006 | Saadat et al. | |
| 2006/0036267 A1 | 2/2006 | Saadat et al. | |

FOREIGN PATENT DOCUMENTS

| | | |
|---|---|---|
| EP | 0 174 843 A1 | 3/1986 |
| EP | 0 246 999 A1 | 11/1987 |
| EP | 0 540 010 A2 | 5/1993 |
| JP | 63277063 A | 11/1988 |
| JP | 63279854 | 11/1988 |
| JP | 63302863 A | 12/1988 |
| JP | 01049572 A | 2/1989 |
| JP | 04297219 | 10/1992 |
| WO | WO 94/18893 A1 | 9/1994 |
| WO | WO 99/17662 A1 | 4/1999 |
| WO | WO 99/53827 A1 | 10/1999 |
| WO | WO 00/32137 A1 | 6/2000 |
| WO | WO 00/48656 A1 | 8/2000 |
| WO | WO 00/78227 A1 | 12/2000 |
| WO | WO 00/78229 A1 | 12/2000 |
| WO | WO 01/66018 A1 | 9/2001 |
| WO | WO 01/67964 A2 | 9/2001 |
| WO | WO 01/85034 A1 | 11/2001 |
| WO | WO 02/24080 A2 | 3/2002 |
| WO | WO 02/35980 A2 | 5/2002 |
| WO | WO 02/39880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 A2 | 1/2003 |
| WO | WO 03/017882 A2 | 3/2003 |
| WO | WO 03/078721 A2 | 9/2003 |
| WO | WO 03/086247 A1 | 10/2003 |
| WO | WO 03/088844 A1 | 10/2003 |
| WO | WO 03/094785 A1 | 11/2003 |
| WO | WO 03/099140 A1 | 12/2003 |
| WO | WO 03/105563 A2 | 12/2003 |
| WO | WO 03/105671 A2 | 12/2003 |
| WO | WO 2004/009269 A2 | 1/2004 |
| WO | WO 2004/014237 A1 | 2/2004 |
| WO | WO 2004/017863 A2 | 3/2004 |
| WO | WO 2004/019787 A2 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A1 | 12/2004 |
| WO | WO 2005/023118 A1 | 3/2005 |
| WO | WO 2005/037152 A1 | 4/2005 |
| WO | WO 2005/058239 A2 | 6/2005 |
| WO | WO 2005/060882 A1 | 7/2005 |
| WO | WO 2006/078781 A1 | 7/2006 |

OTHER PUBLICATIONS

C. Clark, "The Gastric Bubble: Medicine, Magic or Mania?", *SGA J.*, vol. 9, No. 2, 1986, 45-47.

S. L. Edell et al., "Radiographic Evaluation of the Garren Gastric Bubble," *AJR* 145, 1985, pp. 49-50.

S. Gukovsky-Reicher, M.D. et al., "Expandable Metal Esophageal Stents: Efficacy and Safety", Review of Current Literature Data and of 53 Stents Placed at Harbor-UCLA Medical Center, www.medscape.com/viewartcle, 20 pgs. downloaded Aug. 24, 2002.

D. F. Kirby et al., "Incomplete Small Bowel Obstruction by the Garren-Edwards Gastric Bubble Necessitating Surgical Intervention", *The Am. J. of Gastroenterology*, vol. 82, No. 3, 1987, pp. 251-253.

O. G. Nieben et al., "Intragastric ballon as an artificial bezoar for treatment of obesity", The Lancet, Mar. 27, 1982, pp. 198-199.

T. V. Taylor et al., "Gastric Baloons for Obesity", The Lancet, Mar. 27, 1982, p. 750.

W. L. Percival, MD, "The Balloon Diet": a Noninvasive Treatment for Morbid Obesity. Preliminary Report of 108 Patients, *The Canadian J. of Surgery*, vol. 27, No. 2, 1984, pp. 135-136.

Y. Vandenplas et al., "Intragastric balloons in adolescents with morbid obesity", *European J. of Gastroenterology & Hepatology*, vol. 11, No. 3. pp. 243-245.

B. De Waele, MD et al., "Inragastric Balloons for Preoperative Weight Reduction", *Obesity Surgery*, 10, pp. 58-60, 2000.

S. B. Benjamin et al., Abstract, "A Double-Blind Cross Over Study of the Garren-Edwards Anti-Obesity Bubble", *Gastrointestinal Endoscopy*, 1987, Abstract No. 105, vol. 33, No. 2, 1987, p. 168.

S. B. Benjamin, Abstract, "Small Bowel Obstruction and the Garren-Edwards Bubble: Lessons to be Learned?", *Gastrointestinal Endoscopy*, Abstract No. 161, vol. 33, No. 2, 1987, p. 183.

O. W. Cass, Abstract, "Long-Term Follow-Up of Patients with Percutaneous Endoscopic Gastrostomy", *Gastrointestinal Endoscopy*, Abstract No. 162, vol. 33, No. 2, 1987, p. 183.

Büchler, M.W., M.D. et al., A Technique for Gastroplasty as a Substitute for the Esophagus: Fundus Rotation Gastroplasty, *Journal of The American College of Surgeons*, vol. 182, pp. 241-245, Mar. 1996.

Chang, Craig G. M.D., et al., Gastro-Clip® Gastroplasty: A Very Long-Term Complication, *Obesity Surgery*, 14, © FD-Communications Inc.. 2004.

Cummings, David E., M.D., et al., Plasma Ghrelin Levels After Diet-Induced Weight Loss or Gastric Bypass Surgery, *New England Journal of Medicine*, vol. 346, No. 21, pp. 1623-1630, May 23, 2002.

Davenport, Horace W., Ph.D., D.Sc., *Physiology of the Digestive Tract: An Introductory Text*, 3d Ed., Cover and Table of Contents, 1961.

DeMeester, Tom T., M.D., Evolving Concepts of Reflux: The Ups and Downs of the LES, *Canadian Journal of Gastroenterology*, vol. 16, No. 5, pp. 327-331, 2002.

Endo Gia* Universal, Single UseStapler and Endo GIA Roticulator*, Brochure, 8 pages, Undated.

Filipi, Charles J. M.D., et al., Transoral, Flexible Endoscopic Suturing for Treatment of GERD: A Multicenter Trial, *Gastrointestinal Endoscopy*,. vol. 53, No. 4, pp. 416-422, 2001.

Gray, Henry, R.R.S., *Anatomy of the Human Body*, The Digestive System, Thirtieth American Edition, pp. 1466-1467 (Undated).

Guidant, Internet, AXIUS™ VACUUM 2 Stabilizer Systems, Internet Website—www.guidant.com/products/axius_vacuum.shtml, 8 pages, visited May 27, 2003.

Hepworth, Clive C. FRCS et al., Mechanical Endoscopic Methods of Haemostasis for Bleeding Peptic Ulcers: A Review, *Bailliere's Clinical Gastroenterology*, vol. 14, No. 3 pp. 467-476, 2000.

Ikeda, Y. et al., New Suturing Device for Transanal Endoscopic Microsurgery, *Blackwell Science Ltd.* p. 1290, 1997.

Johnson & Johnson Gateway$^{SM}$ Endopath 3mm, 5mm and 10 mm Diameter Endoscopic Instruments, Internet Website—www.inigateway.com/home.ihtml?loc=USENG&page=viewContent&parentId-0900..., 3 pages, visited May 29, 2003.

Power Medical Interventions Digital and Wireless Medical Technology, Product Innovation: SurgASSIST™, Internet Website—www/pmi2.com/access_flexibility.asp, 6 pages, visited May 29, 2003.

Snowden Pencer, Diamon-Flex Angled Snake Retractor (class 1, 878.4800), Appendix F.f, Undated.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D. et al., An Endoscopic Sewing Machine, *Gastrointestinal Edoscopy*, vol. 32, No. 1 pp. 36-38 1986.

Swain, C. Paul, M.D., Endoscopic Sewing and Stapling Machines, *Endoscopy* pp. 205-210, © Georg Thieme Verlag Stuttgart, New York, 1997.

Swain, C. Paul. M.D. et al., An Endoscopic Sewing Machine, *Gastrointestinal Endoscopy*, vol. 32, No. 1, pp. 36-38, 1986.

Swain, C. Paul, M.D. et al., An Endoscopic Stapling Device: The Development of a New Flexible Endoscopically Controlled Device for Placing Multiple Transmural Staples in Gastrointestinal Tissue, *Gastrointestinal Endoscopy*, vol. 35, No. 4, pp. 338-339, 1989.

Swain, C. Paul, M.D., Endoscopic Suturing, *Bailliere's Clinical Gastroenterology*, Bailliere's Tindall,, vol. 13 No. 1, pp. 97-108, 1999.

Vandenplas, Y., et al., Intragastric Balloons in Adolescents With Morbid Obesity, *European Journal of Gastroenterology & Hepatology*, vol. 11, No. 3, pp. 243-245, 1999.

Villar, Hugo V., M.D., et al., Mechanisms of Satiety and Gastric Emptying After Gastric Partitioning and Bypass, *Surgery*, pp. 229-236, Aug. 1981.

Wullstein, C., et al., Compression Anastomosis (AKA-2) in Colorectal Surgery: Results in 442 Consecutive Patients, *British Journal of Surgery 2000*, pp. 1071-1075.

* cited by examiner

US 8,092,482 B2

STENTED ANCHORING OF GASTRIC SPACE-OCCUPYING DEVICES

This is a continuation of U.S. Ser. No. 10/233,236 filed Aug. 30, 2002, which will issue as U.S. Pat. No. 7,033,384 on Apr. 25, 2006.

FIELD OF THE INVENTION

The present invention relates generally to medical apparatus and methods and more particularly to devices and methods for the insertion and securing of expandable devices and the like within a patient's stomach, intestine or gastrointestinal track for purposes of taking up space to provide the patient with a feeling of satiety or fullness. These devices may also be removed once they have served their purpose, e.g., the patient has lost the directed or desired amount of weight.

BACKGROUND OF THE INVENTION

Currently, in cases of severe obesity, patients may undergo several types of surgery either to tie off or staple portions of the large or small intestine or stomach, and/or to bypass portions of the same to reduce the amount of food desired by the patient, and the amount absorbed by the intestinal track. Procedures such as laparoscopic banding, where a device is used to "tie off" or constrict a portion of the stomach, or the placement of intragastric balloons within the stomach can also achieve these results.

Endoscopic procedures that have been used to assist weight loss have been primarily focused on the placement of a balloon or other space occupying device in the patient's stomach to fill portions of the stomach to provide the patient with the feeling of fullness, thereby reducing food intake. To accomplish these procedures, an endoscope is utilized to guide the balloon through the patient's mouth and down the esophagus to the stomach. Usually these procedures have allowed placement of the device for 6-12 months, and are coupled with counseling and other types of psychological support.

In the case of laparoscopic banding or balloon placement, however, several complications can arise that make these procedures, in their present form, clinically suboptimal. The surgical interventions described above require the patient to submit to an intervention under general anesthesia, and can require large incisions and lengthy recovery time. The less invasive procedures described above, although clinically efficacious in many cases, suffer from complications ranging from deflation of the devices resulting in unsustained weight loss, to stomach erosion, bowel obstruction and even death.

Many of these described problems have stemmed from the fact that the devices were not robust enough to sustain long term implantation, and that they were implanted in such a manner as to remain unattached or free-floating within the stomach. Further, due to the caustic nature of stomach acids and other factors, many of the implants deflated and migrated into the intestine, causing bowel obstructions and in some cases death. Also, many devices were not well designed for removal, leading to additional technical difficulties for the clinician.

BRIEF SUMMARY OF THE INVENTION

The present invention provides for improved methods and apparatus for deploying and securing space-occupying devices within the gastrointestinal system of a patient, especially the stomach of the patient, in a minimally invasive manner such as through transesophageal endoscopy. The invention allows greater access to procedures and devices by patients who might not otherwise be treated surgically as "morbidly obese" (at or above a Body Mass Index (BMI) of 40 kg/m3), but who may just be moderately obese or overweight (BMI of between 25 to 40 kg/m3). In addition, patients who require more invasive surgery for an unrelated ailment, may need a minimally invasive way to lose the weight prior to their more invasive procedure, thereby reducing the risks associated with general anesthesia, or otherwise enabling the more invasive procedure.

In particular, the present invention provides for space occupying devices that include a stent configured for deployment in the gastrointestinal tract of a patient, and in particular, for deployment in the esophagus or the stomach. Secured to the stent is an expandable member that is adapted to reside within the gastrointestinal tract and, especially, within the patient's stomach. When expanded, the expandable member occupies a predefined volume within the patient's stomach or gastrointestinal tract.

The present invention also provides for methods and systems for the deploying such space occupying devices.

DETAILED DESCRIPTION OF THE INVENTION

The present invention provides for space occupying devices having an expandable, space-occupying member tethered to an anchoring stent. The stent itself is typically of the self-expanding variety that can be easily deployed within, e.g., a patient's esophagus or stomach, and remain in a generally fixed relationship relative to the patient's stomach cavity. The expandable member is tethered to the stent in a manner allowing the expandable member to reside within the patient's stomach. This system has certain advantages over other known systems, including allowing for a much less traumatic method of anchoring or otherwise retaining the expandable member within the stomach as compared to other systems. For example, methods described in U.S. patent application Ser. No. 09/816,850, filed Mar. 23, 2001, which is commonly owned is and incorporated herein by reference in its entirety, rely on the use of suture or other fastening means that penetrate the stomach wall to anchor an expandable device to the stomach wall. The present invention by contrast avoids compromising the integrity of the stomach wall or gastrointestinal tract in general.

Figure 1:
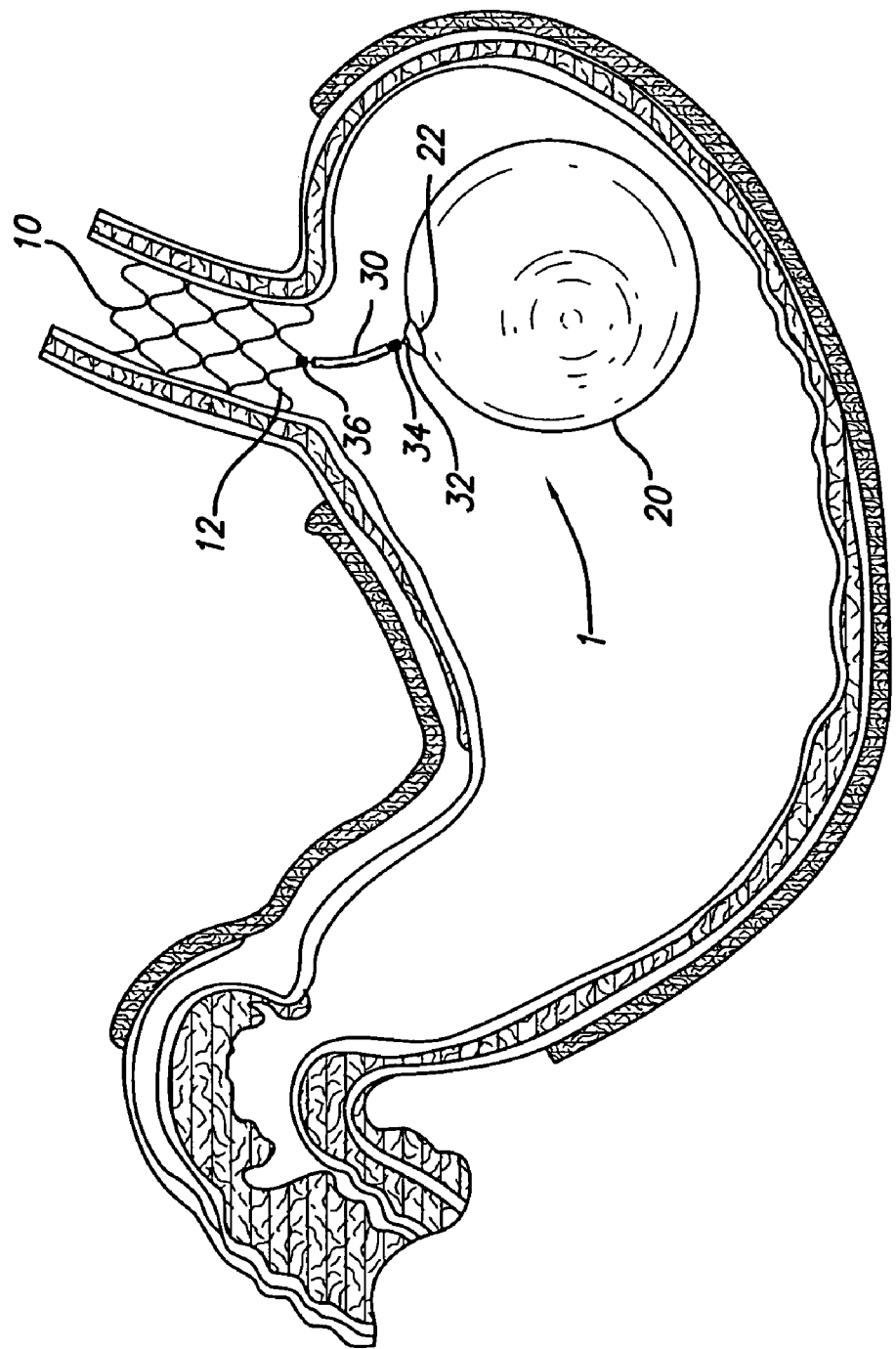
FIG. 1 shows a cross-sectional view of the esophagus and stomach of a patient, with a space occupying device according to the present invention deployed therein, the stent portion of the device being deployed and anchored against the esophagus and the expandable member portion secured to the stent portion and residing within the stomach.

Referring now to FIG. 1, an embodiment of a space occupying device 1 according to the present invention is depicted having anchoring stent 10 and expandable member 20. As shown, anchoring stent 10 is deployed within the esophagus, remaining in a fixed location relative to the stomach. Tether 30 is secured to both anchoring stent 10 and expandable member 20, connecting the two together. Expandable member 20 includes tethering region 22 in the form of a ring or a clasp integral to the member. Distal end 32 of tether 30 is attached to tethering region. Proximal end 36 of tether 30 is attached to anchoring stent 10 at distal end 12 of the anchoring stent. Tether 30 further includes swivel portion 34 located proximal of distal end 32. Swivel portion 34 allows the expandable member to twist or rotate freely without transmitting torque or other rotational forces onto anchoring stent 10. Tether 30 can also be configured with a swivel, rotating joint, or other similar mechanism at proximal end 36 of tether 30 to further relieve torque or rotational strain on stent 10 due to twisting or rotation of expandable member 20.

Stent 10 can be formed in a variety of configurations and of a variety materials known to one skilled in the art. In particular, conventional esophageal stents can be used or readily modified for use in the present invention. Such stents can be of the non-expanding or expanding variety, including those typically used in addressing problems of progressive dysphagia associated with esophageal cancer. Expanding stents include those that are deformable and that are typically expanded using, e.g., a balloon catheter, as well as those that are resilient in nature and that can be delivered in a compressed state and which can self-expand to their original state. Preferably, the stents are of the radially self-expanding variety for ease of deployment in the esophagus. Typically, such stents are made of stainless steel or nitinol (nickel-titanium alloy) and formed into e.g. knitted wire tube, tubular mesh, coiled spring, and like configurations. Suitable self-expanding esophageal metal stents (SEMS) include those sold under the brand names Esophacoil™ (Medtronic/Instent, Eden Prairie, Minn.), Ultraflex™ (Boston Scientific/Microvasive, Natick, Mass.), Wallstent™ (Boston Scientific/Microvasive, Natick, Mass.), and Z-stent™ (Wilson-Cook, Winston-Salem, N.C.). Additional examples of such stents include those described in U.S. Pat. Nos. 5,876,448 and 6,248,058, each of which is incorporated herein by reference in its entirety. Length and diameter of the stent can usually range from 6-15 cm (length) and 16-22 mm (diameter) for most applications. The stents may further be coated, either partially or completely, with e.g. a polymeric film such as silicone.

Expandable member 20 is an inflatable balloon and may be formed of a urethane interior and a silicone exterior. The urethane provides a durability to the balloon for resisting undesirable rupture or leakage and the silicone exterior provides for a smoothness, and conformability to avoid unnecessary trauma or irritation to the stomach lining. In another variation, the expandable member 20 is formed of a composite of silicone, aluminized polyester film, and polyethylene. In this variation, the space occupying device is formed by heat-sealing sheets of mylar/polyethylene composite. The seam is then trimmed to a minimum size and a valve attached. The assembly is then dipped in room temperature vulcanizing (RTV) liquid silicone which, once cured, will leave a smooth surface, which may or may not have a palpable seam. Alternatively, the space occupying device can be rotated as the silicone cures, to allow for a more consistent coating to form. In yet another variation, the balloon is formed of weldable polylolefin films. A variety of sizes and shapes of space-occupying member 30 are contemplated, and it is to be appreciated that one skilled in the art would be competent to choose a particular shape and size according to the particular application. The space-occupying member 30 can be, for example, a spherical or ellipsoidal balloon or another suitable shape. In the case of an ellipsoidal balloon, one method of anchoring such a balloon is along the longer axis of the balloon; however, anchoring may also be achieved by anchoring along the shorter axis of the balloon. Balloon volumes can vary, but a typical volume is approximately 500 cubic centimeters (cc).

Other types of expandable members capable of occupying space within the stomach are also contemplated for use in the present invention. These include, but are not limited to, expandable members such as those described in U.S. patent application Ser. No. 09/816,850, incorporated herein by reference, which include expandable members that can be expanded upon introduction of inflation media or other materials, or through other means including mechanical expansion means. In addition, the expandable member may further incorporate or include materials or markers such that the expandable member is visible under X-ray or other imaging means. Further, the expandable member may include additional surface features, such as a flange, beads, loops, and/or tabs incorporated into the expandable member to facilitate insertion, manipulation, deflation and/or removal of the expandable member.

Tether 30 can be formed of any suitable biocompatible, nonadsorbable material with sufficient strength to withstand the load placed on it by the expandable member. Such materials include, e.g., conventional suture materials, including stainless steel, silk, nylon, polypropylene, and PTFE. The fasteners and swivels provided on the tether can be formed of e.g. stainless steel or a biocompatible plastic.

Deployment of space occupying device 1 can be accomplished by advancing the expandable member 20 into the patient's stomach, and either concurrently or separately deploying the stent 10. For example, an endoscope or like device can be used pass the expandable member 10, in its deflated state, transorally through the patient's mouth and down the esophagus into the patient's stomach (a transesophageal approach). The same delivery device or a separately introduced device can be used to deliver inflation media (e.g., inert gases, such as air, nitrogen, or fluids such as water, saline, etc.) to expand the member to its desired volume. A less desirable method for introducing expandable member 10 into the stomach would be through a percutaneous gastrostomy procedure to create a gastric fistula through which the deflated expandable member could be passed into the stomach and then inflated. These methods are described in further detail in U.S. patent application Ser. No. 09/816,850, which is commonly owned and incorporated herein by reference.

Stent 10 can be deployed according to conventional methods. Rigid or semi-rigid non-expanding stents usually require dilation of the esophagus prior to placement of the stent. Expandable stents that are deformable but non-self expanding are typically deployed through the use e.g. of a balloon catheter that can expand the stent and deploy it in the desired location against the esophageal wall. Resilient or self-expanding stents are usually delivered to the desired location in a radially compressed state. For example, the stent may be introduced into esophagus on a stent delivery device having an outer tube surrounding the stent that maintains the stent in a radially compressed state. Once positioned at the desired location, the outer tube is axially withdrawn, allowing the stent to radially self-expand. An example of such a device is described in U.S. Pat. No. 5,876,448, incorporated herein by reference in its entirety.

Where the expandable member and stent are separately deployed, tether 30 can be coupled to either the expandable member or the stent prior to their deployment. Additional tools deliverable e.g. through an endoscope, such as graspers or snares, can be used to manipulate the tether and engage it at the desired location on the other element, i.e., either stent or expandable member. Alternatively, the tether itself can be configured with a separate connectable element such that the tether is divided into two portions, one of each being attached to either the stent or the expandable member. Once the stent and expandable member are deployed, a grasper, snare, or other tool can used to manipulate the two tether portions to connect them together.

In a particular method of deployment, a single delivery device is used that is capable of simultaneously deploying both the expandable member and the stent. For example, an endoscope or similar device can be configured to retain both an expandable member in its deflated state and a self-expanding stent in its radially compressed state. This can be accomplished, e.g., by the provision of an overtube that extends over the radially compressed stent and that also extends distally of the endoscope to provide a cavity for the deflated expandable member to reside. The endoscope can be advanced transorally through the esophagus to the stomach at which point the overtube can be partially retracted, deploying the expandable member in the stomach. The endoscope can then be manipulated to position the stent in the desired location in the esophagus and the overtube further retracted to release the stent and permit it to radially self-expand into position. As further described in U.S. patent application Ser. No. 09/816,850, which is commonly owned and incorporated herein by reference, an inflation tube may be further provided culminating in e.g. an inflation needle received through a corresponding valve on the expandable member. The inflation tube can be passed through e.g. a lumen located in the delivery device. In this manner, the expandable member can be inflated upon deployment in the stomach.

Once a patient has lost the desired amount of weight, or based on other determining factors, the inflated expandable member can be deflated and removed according to ways such as those described in U.S. patent application Ser. No. 09/816,850, which is commonly owned and incorporated herein by reference. If desired, the stent can also be removed according to known methods. It may in some cases be advantageous to cut or break the tether prior to removal.

Figure 2:
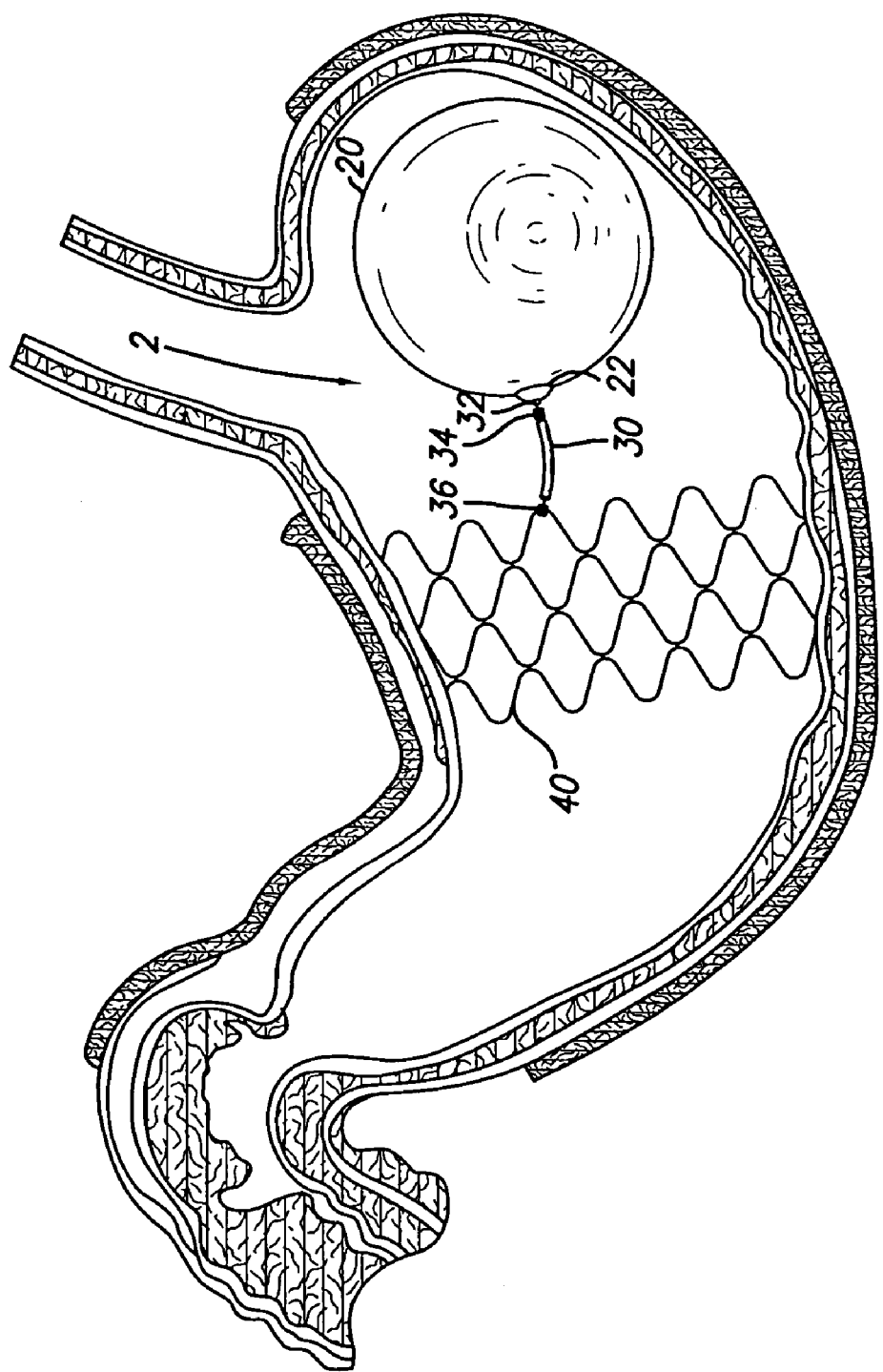
FIG. 2 shows a cross-sectional view of the esophagus and stomach of a patient, with a space occupying device according to the present invention deployed therein, the stent portion of the device being deployed and anchored against the stomach and the expandable member portion secured to the stent portion and residing within the stomach.

FIG. 2 shows another embodiment of the present invention. Space occupying device 2 includes anchoring stent 40 with, expandable member 20 is secured to anchoring stent 40 through tether 30. As can be seen, the embodiment of FIG. 2 is similar to that of FIG. 1 except with anchoring stent 40 being adapted to be deployed and reside within the stomach itself. Stent 40 is preferably an expandable or self-expandable stent of similar construction to that described above with respect to stent 10, but with an expanded diameter the and necessary strength to be positioned and retained within the stomach. The stent can be placed according to ways previously described using a delivery device advanced transesophageally to the desired location in the stomach. Alternatively, the stent can be placed by using percutaneous gastrostomy procedures to create a gastric fistula through which the stent may be passed.

In the embodiments shown in FIGS. 1 and 2, the expandable member is depicted as being located in a spaced apart relationship from the stent. One skilled in the art will appreciate that by adjusting the length of the tether, the location along the stent where the tether is attached, and the particular configuration of the expandable member, one can also achieve orientations of the expandable member where the expandable member is partially, or even fully, disposed within the volume defined by the stent.

Although certain illustrative variations of the present invention are described above, it will be evident to one skilled in the art that various changes and modifications may be made without departing from the invention, and the invention is not intended to be limited by the specifics of any particular variation but is rather defined by the accompanying claims.

We claim:

1. A space occupying device for occupying a volume within a patient's stomach, comprising:
    an expandable stent configured to be implanted in the patient's esophagus or stomach;
    an expandable member having a wall defining a sealed volume therein when expanded, the expandable member also having a tethering region;
    a tether having a distal end and a proximal end; and
    the distal end of the tether being attached to the tethering region on the expandable member and the proximal end of the tether being attached to the stent so that the expandable member resides within the patient's stomach.

2. The space occupying device of claim 1 wherein the stent is configured for deployment in the patient's esophagus.

3. The space occupying device of claim 1 wherein the stent is configured for deployment in the patient's stomach.

4. The space occupying device of claim 1 wherein the stent is a self-expanding stent.

5. The space occupying device of claim 1 wherein the expandable member is inflatable.

6. The space occupying device of claim 1 wherein the distal end of the tether includes a swivel portion attached to the expandable member so that the expandable member is free to twist or rotate in the stomach without transmitting torsional forces to the stent.

7. The space occupying device of claim 1 wherein the stent is configured to be implanted in the patient's pylorus.

8. A space occupying device for occupying a volume within a patient's stomach, comprising: an inflatable member having a tethering region adapted to reside within the patient's stomach and occupy a volume therein when expanded; an expandable stent; and a tether having a distal end secured to the tethering region of the inflatable member and a proximal end attached to the expandable stent.

* * * * *